(12) United States Patent
Matteo et al.

(10) Patent No.: US 9,329,462 B2
(45) Date of Patent: May 3, 2016

(54) PROTON TREATMENT LOCATION PROJECTION SYSTEM

(71) Applicant: ProNova Solutions, LLC, Knoxville, TN (US)

(72) Inventors: Joseph C. Matteo, Walland, TN (US); Jonathan Huber, Knoxville, TN (US)

(73) Assignee: ProNova Solutions, LLC, Knoxville, TN (US)

( * ) Notice: Subject to any disclaimer, the term of this patent is extended or adjusted under 35 U.S.C. 154(b) by 0 days.

(21) Appl. No.: 14/059,527

(22) Filed: Oct. 22, 2013

(65) Prior Publication Data

US 2014/0114113 A1    Apr. 24, 2014

Related U.S. Application Data

(60) Provisional application No. 61/716,831, filed on Oct. 22, 2012.

(51) Int. Cl.
*G01J 1/00* (2006.01)
*G03B 21/14* (2006.01)
*A61N 5/10* (2006.01)

(52) U.S. Cl.
CPC .............. *G03B 21/14* (2013.01); *A61N 5/1043* (2013.01); *A61N 2005/1056* (2013.01); *A61N 2005/1087* (2013.01)

(58) Field of Classification Search
CPC ............................................. A61N 2005/1087
USPC ................................. 250/491.1, 492.1, 492.3
See application file for complete search history.

(56) References Cited

U.S. PATENT DOCUMENTS

| | | | |
|---|---|---|---|
| 5,376,007 A | * | 12/1994 | Zirm .............................. 434/262 |
| 6,429,578 B1 | | 8/2002 | Danielsson et al. |
| 6,780,149 B1 | | 8/2004 | Schulte |
| 6,841,784 B2 | | 1/2005 | Brahme et al. |
| 6,865,254 B2 | | 3/2005 | Nafstadius |
| 6,891,166 B2 | | 5/2005 | Brahme et al. |
| 6,969,194 B1 | | 11/2005 | Nafstadius |
| 7,120,223 B2 | | 10/2006 | Nafstadius |
| 7,400,434 B2 | | 7/2008 | Brahme et al. |
| 7,693,256 B2 | | 4/2010 | Brahme et al. |
| 7,826,593 B2 | | 11/2010 | Svensson et al. |
| 8,235,530 B2 | | 8/2012 | Maad |
| 2003/0147495 A1 | * | 8/2003 | Kato ...................... A61N 5/103 378/65 |
| 2007/0284543 A1 | | 12/2007 | Rockseisen |
| 2008/0051773 A1 | * | 2/2008 | Ivanov .................. A61N 5/0616 606/12 |
| 2008/0191142 A1 | | 8/2008 | Pedroni |
| 2009/0076380 A1 | | 3/2009 | Thierman |
| 2009/0189095 A1 | * | 7/2009 | Flynn et al. ................. 250/492.3 |

(Continued)

OTHER PUBLICATIONS

Patent Cooperation Treaty; Int'l Search Report; Form PCT/ISA/220; Date of Mailing: Mar. 10, 2014.

*Primary Examiner* — Nicole Ippolito
*Assistant Examiner* — Jason McCormack
(74) *Attorney, Agent, or Firm* — Pitts & Lake, P.C.

(57) ABSTRACT

Treatment volume projection systems and methods for use in treating patients, including an image scanner to capture an image of a patient's treatment volume, a processor to process the image to generate a treatment volume image corresponding to at least a portion of the treatment volume, and an image projector to project the treatment volume image onto a projection surface. The treatment volume image can include an x-y scanning area of the treatment volume to assist delivery of treatment to the patient.

18 Claims, 4 Drawing Sheets

(56) References Cited

U.S. PATENT DOCUMENTS

| | | | |
|---|---|---|---|
| 2009/0252287 A1* | 10/2009 | Boese et al. | 378/17 |
| 2010/0069758 A1* | 3/2010 | Barnes et al. | 600/473 |
| 2010/0266100 A1* | 10/2010 | Balakin | 378/65 |
| 2011/0249088 A1* | 10/2011 | Hannibal et al. | 348/43 |
| 2011/0306863 A1 | 12/2011 | Koshnitsky et al. | |
| 2012/0001085 A1* | 1/2012 | Fujimoto | A61N 5/103 250/396 ML |
| 2012/0226152 A1* | 9/2012 | Porikli | A61B 5/1114 600/427 |

* cited by examiner

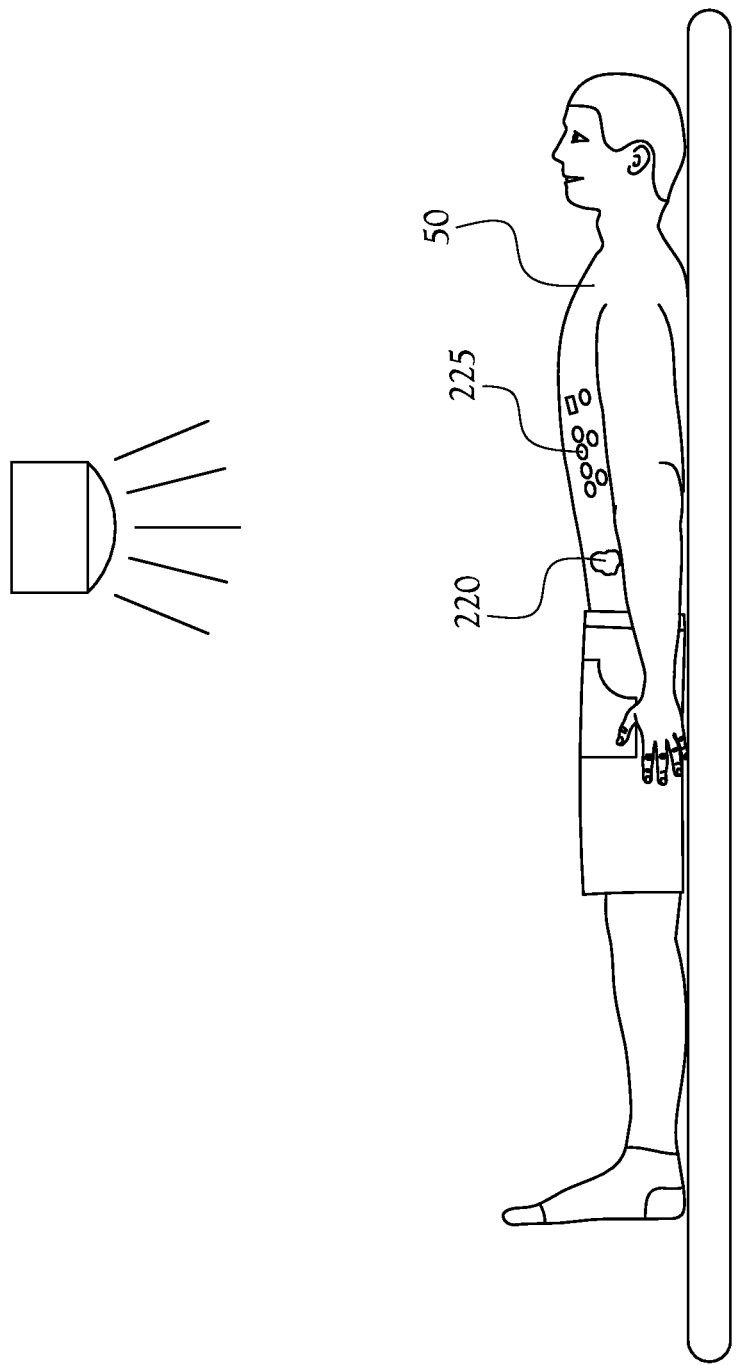

PROTON TREATMENT LOCATION PROJECTION SYSTEM

CROSS-REFERENCE TO RELATED APPLICATIONS

This application claims the benefit of U.S. Provisional Application No. 61/716,831, filed on Oct. 22, 2012.

FIELD OF INVENTION

The present inventive concept relates generally to proton therapy for cancer treatment, and more particularly to systems and methods of projecting projects an image, such as that of a treatment volume, onto a patient or other projecting surface for use in particle therapy treatment.

BACKGROUND

Proton Therapy (PT) is a cancer treatment technology that uses high energy protons to penetrate a patient's body and deposit energy into treatment volumes such as cancerous tumors. PT leverages the Bragg Peak property of charged particles where they deposit the majority of the energy in the last few millimeters of travel as opposed to conventional radiation therapy where the majority of energy is deposited in the first few millimeters of travel—which often causes significant damage to healthy tissue.

PT is delivered to patients through a series of treatments, which frequently occur every day for several weeks. Each treatment typically requires an anatomical image to verify that the tumor is in the correct position prior to treatment, which may be done with basic planar x-ray technology. The most common beam delivery technique is double scattering where a narrow proton beam is scattered to spread the protons physically and also to create an energy spread such that the protons are traveling at various energies. A collimator may be used to trim the proton treatment area in x and y dimensions, and a compensator may be used to modify the proton treatment in the z dimension. The protons are trimmed to the shape of the tumor to precisely deliver the radiation dose to the treatment volume, while sparing the surrounding healthy tissue.

In contrast, a more advanced technique that is gaining popularity is Pencil Beam Scanning ("PBS"), which eliminates the beam scattering, collimator, and compensator. In PBS treatments, the narrow proton beam is directed by a scanning magnet to follow the treatment shape in the x and y dimensions. The beam is adjusted in the z dimension by varying the energy with an energy degrader, frequently positioned between the scanning magnet and the particle accelerator, such as a cyclotron, generating the proton beam.

BRIEF SUMMARY

Example embodiments of the present general inventive concept provide a proton treatment volume projection system to assist in patient treatment, whereby a projector source provides an image on a patient, proximate a treatment volume, that corresponds to the x and y dimensions of the patient's treatment volume. The treatment can include, but is not limited to, proton therapy treatment.

Example embodiments of the present general inventive concept can also be achieved by providing a treatment volume projection system, including means capable of receiving a particle beamline from a particle beamline generating source and to redirect the particle beamline to a treatment volume contained within a patient, and a means for projecting an image corresponding to at least a portion of the treatment volume onto a projecting surface.

The projecting surface can be one of more of the patient's skin, a wall of a treatment room, and a screen provided to a gantry.

The projected image can be a two-dimensional image corresponding to an x-y scan area projected onto the patient' skin from any angle.

One or more of a directional mirror, light tube, and off-beam-line-axis projector can be provided to direct the projected image onto the projecting surface.

The projected image can include a plurality of treatment volume profiles. The projected image can include at least one of an alignment marker, a patient identifier, a system status indicia, and entertainment/media content.

A camera unit can be provided to record images of the projection surface.

A processor can be provided to process a recorded image using computer vision to perform a three-dimensional isocenter positioning operation.

An actuator can be provided to move the means for projection into the particle beamline for projection of the image, and to subsequently remove the means for projection from the particle beamline during treatment of the patient.

The projected image can be a moving image configured to simulate a scan of the treatment volume.

The projected image can include a first color to indicate that movement by the patient is permitted and a second color to indicate that movement by the patient is prohibited.

The projected two-dimensional image can includes a video of at least one of a physician and support staff.

Example embodiments of the present general inventive concept can also be achieved by providing a method of projecting an image of a patient's treatment volume onto the patient to aid in treatment of the patient, including capturing a first image of a patient's treatment volume, processing the image to generate a treatment volume image corresponding to at least a portion of the treatment volume, projecting the treatment volume image onto the skin of the patient proximate the treatment volume using an image projector, and delivering treatment to the patient's treatment volume according to dimensions of the projected treatment volume image.

The treatment of the patient can include proton pencil-beam-scanning of the patient, and the method can further include moving the image projector into a beamline of a proton delivery system to project the image onto the skin of the patient proximate the treatment volume, and removing the image projector from the beamline during pencil-beam-scanning treatment of the patient.

The projecting operation can include directing the projected treatment volume image using one or more of a mirror, a light tube, and off-beamline projector.

Example embodiments of the present general inventive concept can also be achieved by providing a treatment volume projection system for use in treating patients, including an image scanner to capture an image of a patient's treatment volume, a processor to process the image to generate a treatment volume image corresponding to at least a portion of the treatment volume, and an image projector to project the treatment volume image onto a projection surface.

The system may include a pencil-beam-scanning apparatus to deliver pencil-beam-scanning treatment to a patient, and an actuator to move the image projector into a beamline of the pencil-beam-scanning apparatus for projection of the image to the skin of the patient proximate the treatment volume, and to subsequently remove the image projector from the beamline during pencil-beam-scanning treatment of the patient.

The treatment volume image can include an x-y scanning area of the treatment volume.

The system may further include a camera unit to capture a secondary image from the projected treatment volume image, a confirmation unit to confirm a patient setup by comparing the secondary image to anatomical or optical landmarks/markers.

The projection surface can be the skin of the patient proximate the treatment volume.

Additional features and embodiments of the present general inventive concept will be set forth in part in the description that follows and, in part, will be obvious from the description, or may be learned by practice of the general inventive concept.

BRIEF DESCRIPTION OF THE DRAWINGS

The following example embodiments are representative of example techniques and structures designed to carry out the features of the present general inventive concept, but the present general inventive concept is not limited to these example embodiments. Moreover, in the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 6 illustrates in partial perspective view an example embodiment of the present general inventive concept in which a computer-generated image is provided to the patient proximate the treatment volume.

DETAILED DESCRIPTION

Reference will now be made to example embodiments of the present general inventive concept, examples of which are illustrated in the accompanying drawings and illustrations. The example embodiments are described herein in order to explain the present general inventive concept by referring to the figures.

Embodiments of the present general inventive concept provide a proton treatment volume projection system to be used in proton therapy treatment, whereby a projector source provides an image on a patient, proximate a treatment volume, that corresponds to the x and y dimensions of the patient's treatment volume.

Figure 1:
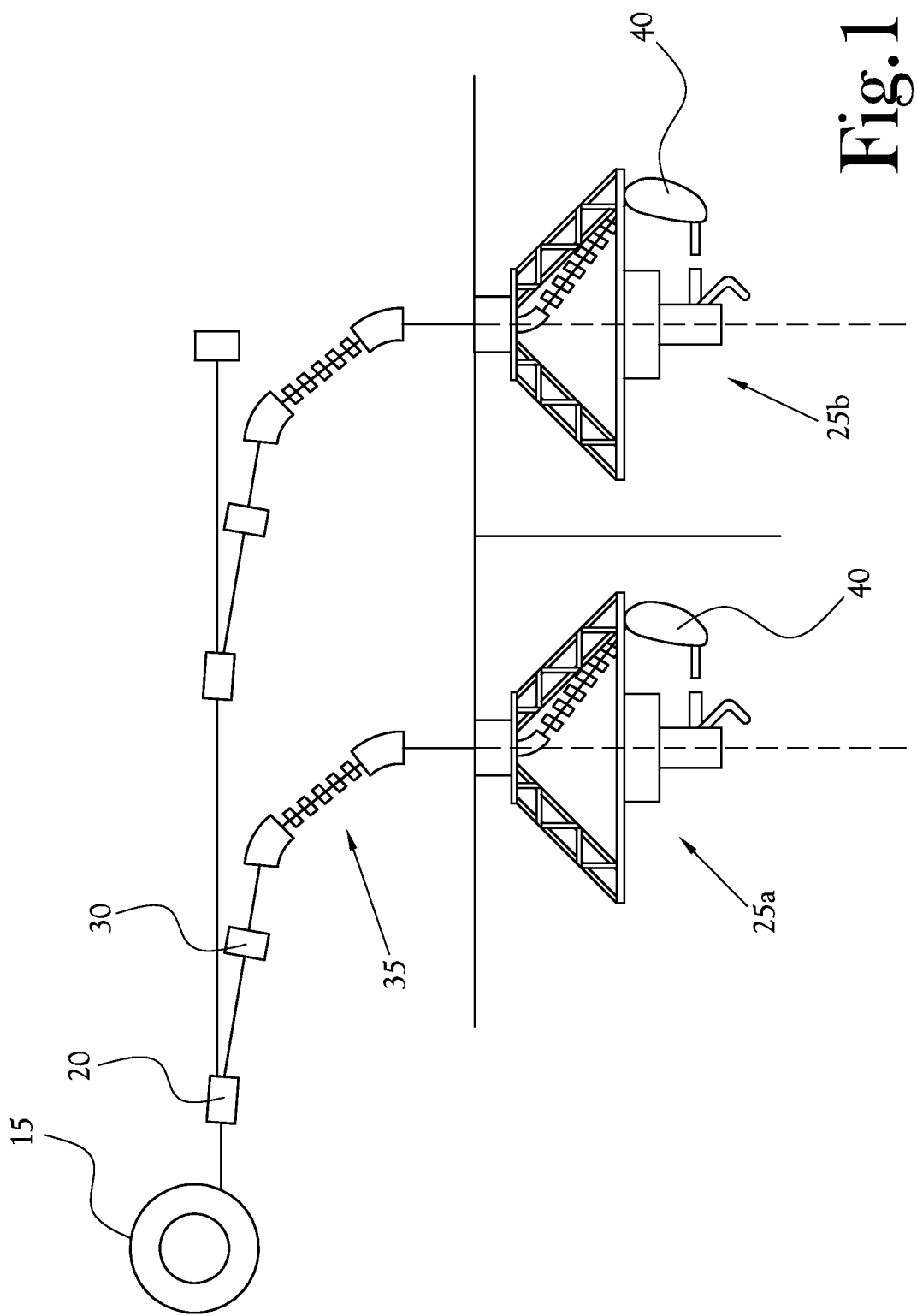
FIG. 1 illustrates, in partial schematic view, an example embodiment proton therapy treatment system whereby adjacent treatment rooms may receive a proton beamline originating at a cyclotron.

Referring now to FIG. 1, protons are generated in a particle accelerator, such as cyclotron 15, and directed to a patient in the form of a beamline through a series of magnets 20 that guide and shape the beamline to match the dimensions of the treatment volume 60. Often two or more treatment rooms 25A and 25B are connected to a single accelerator 15 as shown in FIG. 1. Protons are degraded to the desired energy to penetrate the patient's body and stop in the tumor. An energy selection system (ESS) 35 is often used to filter out various proton energies that are produced by the degrader 30 and only pass along a narrow band of energies for treatment. Inside the treatment room is the final focusing and energy distribution instruments, shown in partial schematic view in treatment rooms 25A and 25B, necessary for precise tumor therapy. The beam can be directed immediately to the patient, but a more common approach is to use a gantry device 40 that redirects the protons 90 degrees so they are perpendicular to the gantry's axis of rotation. This allows protons to be directed to the patient from any angle zero to 360 degrees and allows the physician to design a treatment plan that reduces radiation damage to critical organs and/or healthy tissue.

Figure 2:
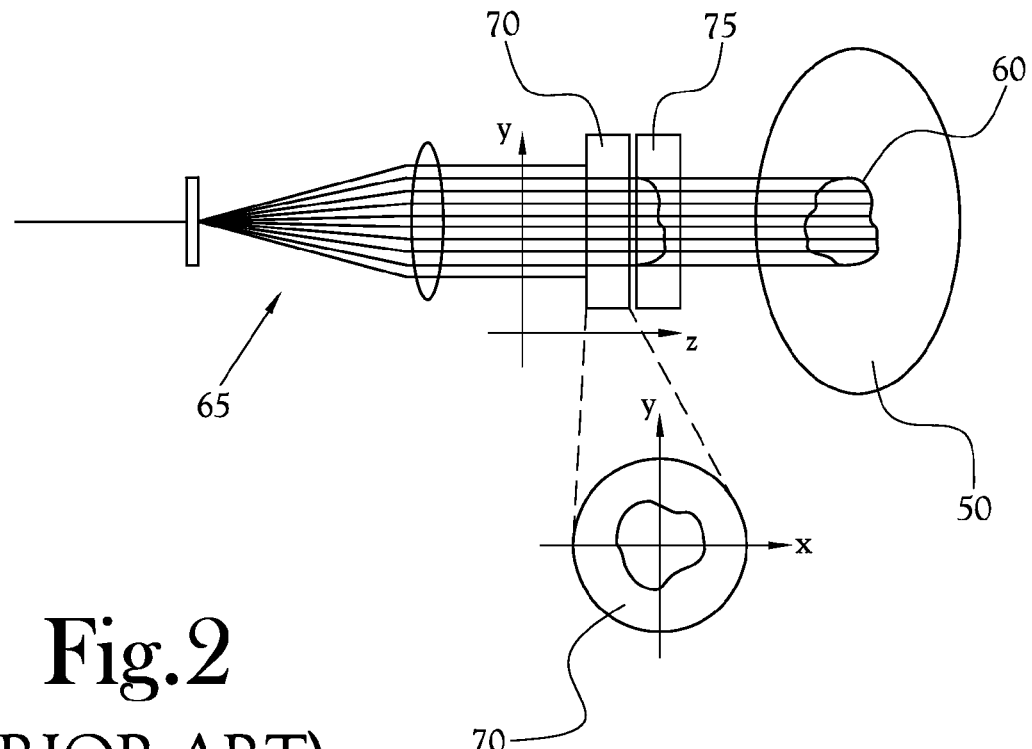
FIG. 2 illustrates a prior art proton therapy treatment system whereby a collimator and a compensator are used to modify the beamline prior to its delivery to a patient.

A common beam delivery technique is to use double scattering 65 in the delivery nozzle near the patient 50 to create an evenly dispersed pattern of protons that are then trimmed in the x and y direction by a collimator 70, typically made of brass, as shown in FIG. 2. A second device, the compensator 75, which is typically made of plastic, is machined in the z direction to change the thickness of plastic that the protons travel through to match the distal shape of the treatment volume 60. The combination of these components allows a treatment protocol that precisely matches the dimensions of the desired treatment volume 60.

Figure 3:
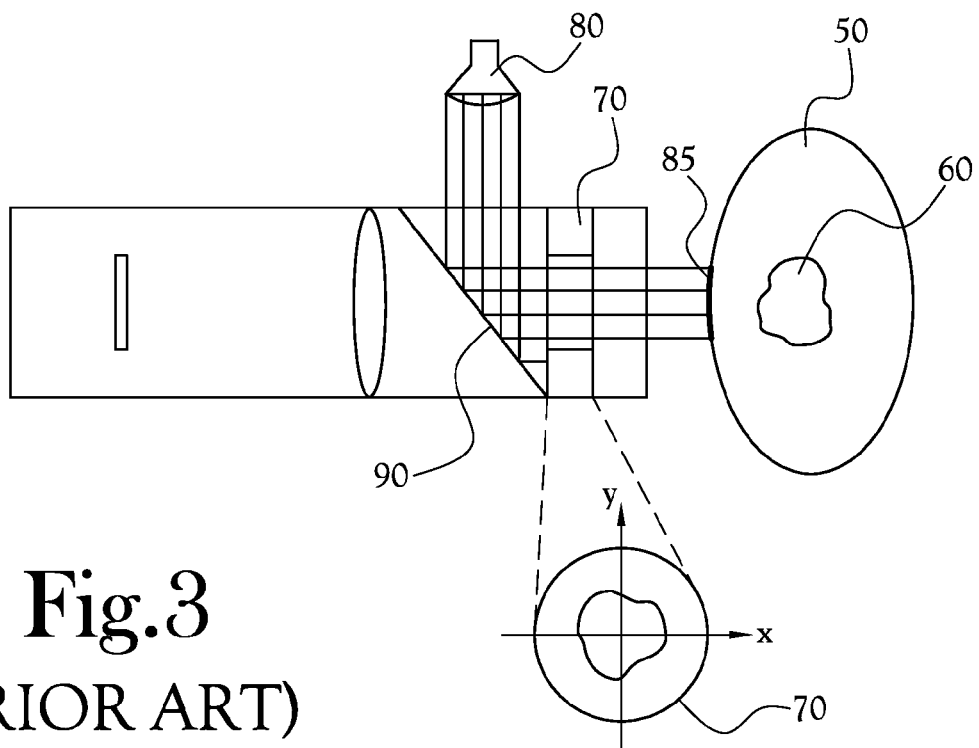
FIG. 3 illustrates the prior art system of FIG. 2, further depicting a projected light source provided to the collimator.

Now referring to FIG. 3, a tool that is often used to help verify treatment alignment and the proper collimator selection is a simple projected light source 80 that shines through the collimator 70 and projects a shaped image 85 onto the patient 50, shown in FIG. 3. The collimator 70 shapes the projected image 85 and helps the treatment physician to quickly identify the treatment volume 60 shape in the x and y dimensions. A retracting mirror 90 used to bring the light from light source 80 in from a perpendicular direction projects it in the direction of the proton beamline.

Figure 4:
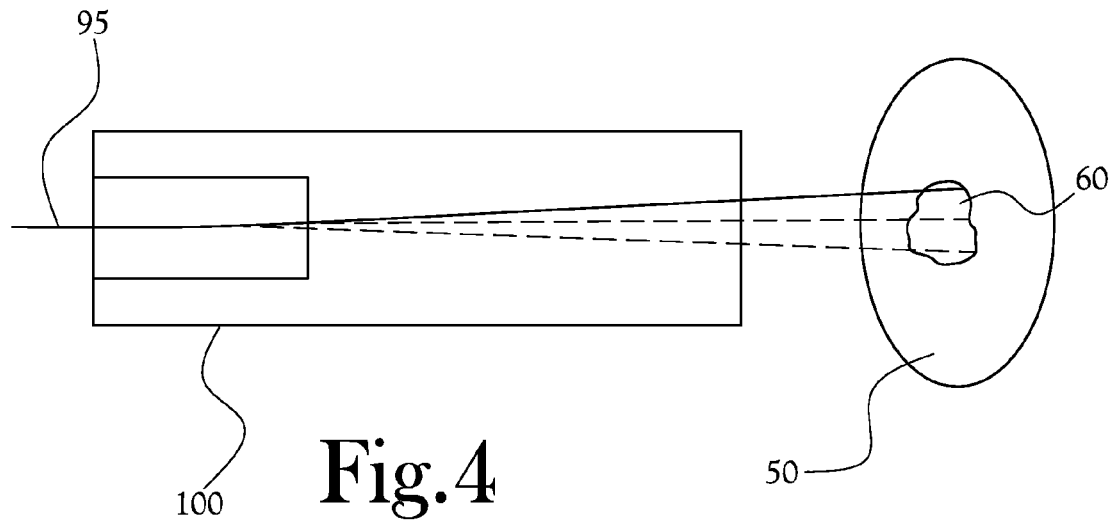
FIG. 4 illustrates another embodiment prior art proton therapy treatment system frequently utilized with PBS to direct the beamline in the x and y dimensions prior to its delivery to a patient.

A more progressive proton therapy treatment technique is spot scanning or pencil beam scanning (PBS) where a narrow beam 95 of protons is deflected by a scanning magnet 100 in the x and y directions while the beam energy, which corresponds to treatment depth (z), is changed prior to the scanning magnet 100, as shown in FIG. 4. This type of treatment technique has many different delivery protocols where a partial dose can be delivered in layers and repainted over the entire treatment volume 60 many times. Another approach is to deliver each layer with the full dose before moving to the next layer. There are also other hybrid techniques as this is currently a very active area of proton therapy development. Typical of these techniques, a collimator and compensator are not used and thus the ability to use a simple light source 80 and project the x-y treatment area is not possible as described earlier. Thus, it will be recognized by those skilled in the art that a treatment volume projection system for use with PBS is currently desired.

Figure 5:
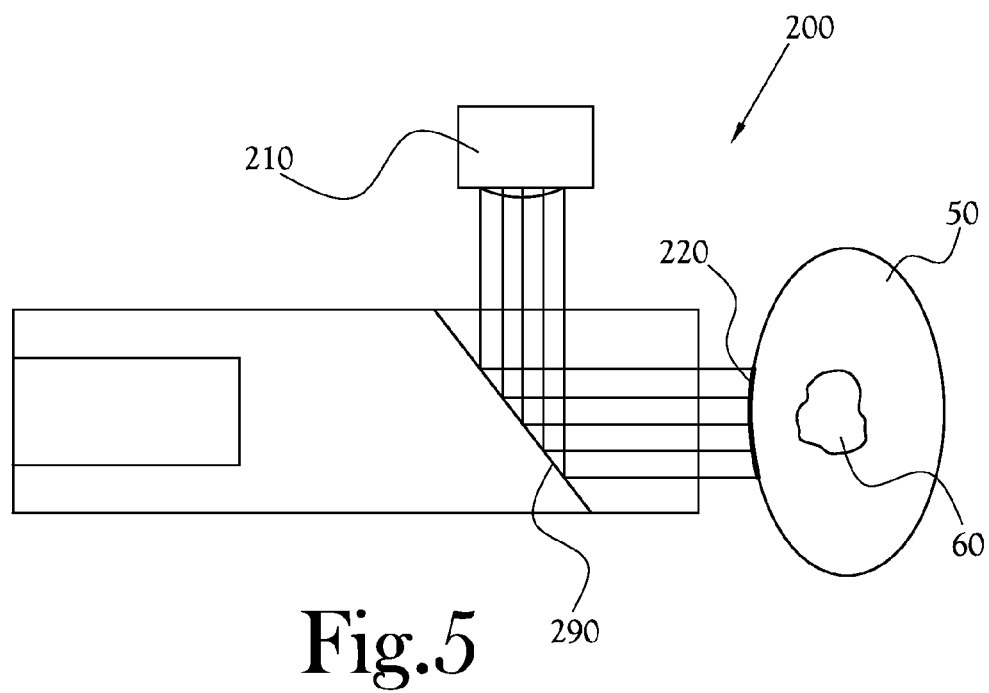
FIG. 5 illustrates an example embodiment of the present general inventive concept whereby a computer-generated image is provided to the patient, proximate the treatment volume.

Now referring to FIGS. 5 and 6, an example embodiment proton treatment volume projection system 200 uses a projector source 210 to project a computer-generated image 220 of the x-y scan area corresponding to the treatment volume 60 on the patient 50. The currently illustrated example embodiment also includes a mirror 290, similar to FIG. 3. A computer generated image 220 that is created directly from an image scanner, such as a CT scanner (not shown), and the scan pattern to be used for delivering the dose is projected onto the patient 50, proximate their treatment volume 60. In one embodiment, the projected x-y scan area corresponds to the largest area of the treatment volume 60. In another embodiment, the computer-generated image 220 of the projected x-y scan area simulates the layer by layer scan process to allow the treatment physician to verify the treatment volume at each layer. The projector 210 could also be used to project alignment markers as well as patient identifiers 225 all contributing to patient safety.

In some embodiments, the x-y scan area/image 220 is projected onto the patient's skin from any angle. In this regard, it will be readily recognized by those skilled in the art that the image 220 could be projected off-axis from beam 95 so as to eliminate the need for mirror 290. It will be further recognized that any type of light guide, such as a fiber optic device, could be used in place of mirror 290. In this regard, in some embodiments, the projector 210 is actuated/moved onto the path of the beamline for projection of the image 220 and subsequently removed from the beamline's path for treatment by an actuator (not shown). In some embodiments, the system includes both a projector 210 and a camera mounted to the actuator. In some embodiments, the image 220 is a single x-y profile/layer, whereas in other embodiments the image 220 includes multiple x-y profiles/layers.

In still other embodiments of the present general inventive concept, the image 220 may be a moving image to simulate a scan of the treatment volume 60. In some embodiments, the image 220 may be projected during treatment and recorded by an external camera. For example, the projected image may be read-back to image what is seen in the beams eye view. This can be used as a quality assurance (QA) tool for use, among other purposes, to confirm patient setup. For example, the therapy physician/support staff in the control room could view the secondary image captured by an external camera to confirm anatomical or optical landmarks/markers.

In another embodiment, the image communicates instructions to the patient 50. For instance, a projected glow of one color (e.g., green) may be provided to indicate that movement is allowed, and a projected glow of another color (e.g., red) may be provided to indicate that movement is prohibited. Additionally, system status indicia, video feeds of the therapy physician/support staff in the control room, and/or entertainment/media content may be projected onto the patient 50, against the wall of a treatment room, and/or against a screen actuated from the gantry 40.

In at least one example embodiment, a grid or other visual alignment marker arrangement is projected onto the patient 50 and then recorded by an external camera and processed using computer vision to perform an initial three-dimensional isocenter positioning operation. It will be appreciated by those skilled in the art that while the present invention has been described in relation to PBS, the treatment volume projection system 200 of the present system has utility with regard to other treatment protocols where the treatment volume is not directly visible to the treating physician or surgeon, such as is the case with laproscopic surgery or surgical techniques such as Gamma Knife or Cyber Knife techniques (Gamma Knife and Cyber Knife are each registered trademarks).

It is also noted that numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Accordingly, while the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A treatment volume projection system, comprising:
   a means capable of receiving a particle beamline from a particle beamline generating source and to redirect the particle beamline to a treatment volume contained within a patient; and
   a means for projecting an image corresponding to at least a portion of the treatment volume, and a scan pattern to be used to deliver the particle beamline to the at least a portion of the treatment volume, onto the patient's skin such that the particle beamline is deliverable to the at least a portion of the treatment volume so as to match dimensions of the projected image and the scan pattern.

2. The treatment volume projection system of claim 1, wherein the projecting surface further includes at least one of a wall of a treatment room, and a screen provided to a gantry.

3. The treatment volume projection system of claim 2, wherein the projected image is a two-dimensional image corresponding to an x-y scan area projected onto the patient' skin from any angle.

4. The treatment volume projection system of claim 1, further including one or more of a directional mirror, a light tube, and off-axis projector to direct the projected image onto the projecting surface.

5. The treatment volume projection system of claim 1, wherein the projected image includes a plurality of treatment volume profiles.

6. The treatment volume projection system of claim 1, wherein the projected image includes at least one of an alignment marker, a patient identifier, a system status indicia, and entertainment/media content.

7. The treatment volume projection system of claim 1, further comprising a camera disposed to record images of the projection surface.

8. The treatment volume projection system of claim 7, further comprising a processor to process a recorded image using computer vision to perform a three-dimensional isocenter positioning operation.

9. The treatment volume projection system of claim 1, wherein the projected image is a moving image configured to simulate a scan of the treatment volume.

10. The treatment volume projection system of claim 1, wherein the projected image includes a first color to indicate that movement by the patient is permitted and a second color to indicate that movement by the patient is prohibited.

11. The treatment volume projection system of claim 1, wherein the projected two-dimensional image includes a video of at least one of a physician and support staff.

12. A treatment volume projection system for use in treating patients, comprising:
- an image scanner to capture an image of a patient's treatment volume;
- a processor to process the image to generate a treatment volume image corresponding to at least a portion of the treatment volume; and
- an image projector to project the treatment volume image and a scan pattern to be used to deliver a treatment to the patient's treatment volume onto the patients skin such that the treatment is deliverable to the treatment volume so as to match dimensions of the projected image and the scan pattern.

13. The system of claim 12, further comprising:
- a camera unit to capture a secondary image from the projected treatment volume image; and
- a confirmation unit to confirm a patient setup by comparing the secondary image to anatomical or optical landmarks/markers.

14. The system of claim 12, wherein the projection surface is the skin of the patient proximate the treatment volume.

15. A treatment volume projection system, comprising:
- means capable of receiving a particle beamline from a particle beamline generating source and to redirect the particle beamline to a treatment volume contained within a patient;
- a means for projecting an image corresponding to at least a portion of the treatment volume onto a projecting surface; and
- an actuator to move the means for projecting an image into the particle beamline for projection of the image, and to subsequently remove the means for projecting an image from the particle beamline during treatment of the patient.

16. A treatment volume projection system for use in treating patients, comprising:
- a pencil-beam-scanning apparatus to deliver pencil-beam-scanning treatment to a patient;
- an image scanner to capture an image of a patient's treatment volume;
- a processor to process the image to generate a treatment volume image corresponding to at least a portion of the treatment volume;
- an image projector to project the treatment volume image onto a projection surface; and
- an actuator to move the image projector into a beamline of the pencil-beam-scanning apparatus for projection of the treatment volume image to the skin of the patient proximate the treatment volume, and to subsequently remove the image projector from the beamline during pencil-beam-scanning treatment of the patient.

17. A treatment volume projection system, comprising:
- a particle beamline generating source configured to direct a particle beamline to a treatment volume contained within a patient; and
- an image projector configured to project an image corresponding to the treatment volume, and a scan pattern to be used to deliver the particle beamline to the treatment volume, onto a projecting surface of the patient such that the particle beamline is deliverable to the treatment volume through the projecting surface according to dimensions of the projected image and the scan pattern.

18. The system of claim 16, wherein the treatment volume image includes an x-y scanning area of the treatment volume.

* * * * *